United States Patent [19]

Moore

[11] Patent Number: Plant 6,678

[45] Date of Patent: Mar. 21, 1989

[54] CHOCTAW BLACKBERRY

[75] Inventor: James N. Moore, Fayetteville, Ark.

[73] Assignee: University of Arkansas, Fayetteville, Ark.

[21] Appl. No.: 118,622

[22] Filed: Nov. 9, 1987

[51] Int. Cl.[4] ..... A01H 5/03

[52] U.S. Cl. ..... Plt./46

[58] Field of Search ..... Plt./46

*Primary Examiner*—Robert E. Bagwill

[57] ABSTRACT

Description and specifications of a new and distinct blackberry variety which originated from seed produced by a hand-pollinated cross of Arkansas Selection 526 (non-patented) and Rosborough (non-patented) is provided. This new blackberry variety can be distinguished by its very early fruit ripening, very erect cane growth habit, small seed size, and excellent fruit quality.

2 Drawing Sheets

SUMMARY OF THE INVENTION

The new and distinct variety of blackberry originated from a hand-pollinated cross of Arkansas Selection 526 (non-pantnted)×Rosborough (non-patented) made in 1975 at the Arkansas Agricultural Experiment Station Fruit Substation at Clarksville, Ark. The seeds resulting from this controlled hybridization were germinated in a greenhouse in the spring of 1976 and planted in a field on the Arkansas Agricultural Experiment Station at Clarksville, Ark. The seedlings fruited during the summer of 1978 and one, designated Ark. 876, was selected for its very early ripening, erect growth habit, and high productivity.

During 1979, the original plant selection was propagated asexually from root cuttings and a test row of 20 plants was established with asexually multiplied plants at four additional locations in Arkansas and on state experiment stations in New York, Florida, Texas, and Louisiana.

The new variety has been asexually multiplied annually since 1979 by the use of root cuttings and by rooting softwood cuttings. It forms new plants from adventitious buds on root cuttings readily and also roots well from softwood cuttings. During all asexual multiplication, the characteristics of the original plant have been maintained and no aberrant phenotypes have appeared.

Test plantings over a wide geographic area have shown this new variety to be adapted to differing soil and climatic conditions. It has performed well in tests in the southern areas of the U.S. but is not coldhardy in northern states.

Plants of the new variety are highly vigorous and prolific and row establishment following planting is rapid. Both primocanes and floricanes are very erect and the fruit is readily accessible to both machine and hand harvest. Thorn size and density are medium, similar to Cherokee and Cheyenne varieties. Plants and fruit are moderately tolerant to anthracnose (*Elsinoe veneta* (Burkh.) Jenkins), and plants are immune to orange rust (*Gymnoconia peckiana* (Howe) Trott), but are occasionally attacked by powdery mildew (*Sphaerotheca humuli* (DC.) Bunn.).

Fruit of the new variety ripens very early, about 7 days before the Cheyenne variety. Average ripening date is May 25 in central Arkansas. The harvest period is shorter than most other erect varieties. The average last harvest date in central Arkansas is June 18. Yields have been equal to the Cheyenne variety but have averaged slightly less than Shawnee.

The fruit is short conic in shape, bright black in color and medium large in size (ca. 5.5 g). The fruit is moderately firm at maturity, being equal to that of the Cheyenne variety, but slightly less firm than Shawnee.

The fresh fruit has been rated as having flavor superior to both Cheyenne and Shawnee. Fruit processed by canning is of very good quality, being superior to both Cheyenne and Shawnee. Seed size is significantly smaller than both Cheyenne and Shawnee.

Fruit clusters are medium-large, cymose, and are borne on the periphery of the plant canopy, providing easy access to harvest. Flower fertility is high and clusters are well filled.

The new variety has been named the Choctaw cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blackberry. Color terminology is in accordance with that of the Royal Horticultural Society Colour Chart published in 1966 by The Royal Horticultural Society of London, England.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Large, very erect.

*Growth.*—Very vigorous; prolific suckering from roots and crowns.

*Productivity.*—High yields, very early ripening; consistent from year to year.

*Cold hardiness.*—Medium, similar to Cheyenne.

*Canes.*—Very erect. Cane diameter: base 1.7 cm, midpoint 1.3 cm, terminal 0.2 cm. Internode length: base 12.5 cm, midpoint 12 cm, terminal 8 cm. Thorn density (per 30 cm): base 17.0, midpoint 21.0, terminal 65.0. Floricane color: base Greyed-Orange Group (165B), midpoint Greyed-Orange Group (165B), terminal Yellow-Green Group (146B). Primocane color: Base Yellow-Green Group (146B), midpoint Yellow-Green Group (146B), terminal Yellow-Green Group (146D). Date of first emergence March 22.

*Disease resistance.*—Moderate for anthracnose; immune to orange rust; occasionally susceptible to powdery mildew.

Foliage:

*Leaves.*—Large. Mature leaf diameter 4.6 cm, length 7.3 cm. Color: Floricane base Green Group (139A), midpoint Green Group (139A), terminal Green Group (139B); Primocane base Green Group (139A), midpoint Green Group (139A), terminal Green Group (137A).

Flowers:

*Date of first bloom.*—April 5.

*Date of full bloom.*—April 14.

*Date of last bloom.*—May 1.

*Blossom color.*—White Group (155C).

*Reproductive organs.*—Stamens — erect, numerous. Pistils — numerous. Pollen — Normal and abundant.

Fruit:

*Maturity.*—Very early, 7 days before Cheyenne. Average ripe date May 25. Average period of maturity May 25–June 18.

*Size.*—Medium large, average 5.5 g, uniform.

*Shape.*—Short conic, uniform.

*Color.*—Glossy black, Black Group (202A).

*Skin.*—Medium tender.

*Drupelet size.*—Small.

*Seed size.*—Small, average 2.1 mg.

*Firmness.*—Good, equal to Cheyenne.

*Flavor.*—Very good, mildly acid.

*Soluble solids.*—9.7%.

*pH.*—3.01.

*Total acids.*—1.116%.

*Processed quality.*—Very good, superior to Cheyenne and Shawnee.

*Uses.*—Fresh and processed, jellies, jams.

The variety: The most distinctive features of the variety are its very early ripening, very erect cane growth habit, small seed size, and high fresh and processed fruit quality.

I claim:

1. A new and distinct variety of blackberry, substantially as illustrated and described, characterized by its very early ripening, very erect cane growth habit, small seed size and excellent fruit quality.

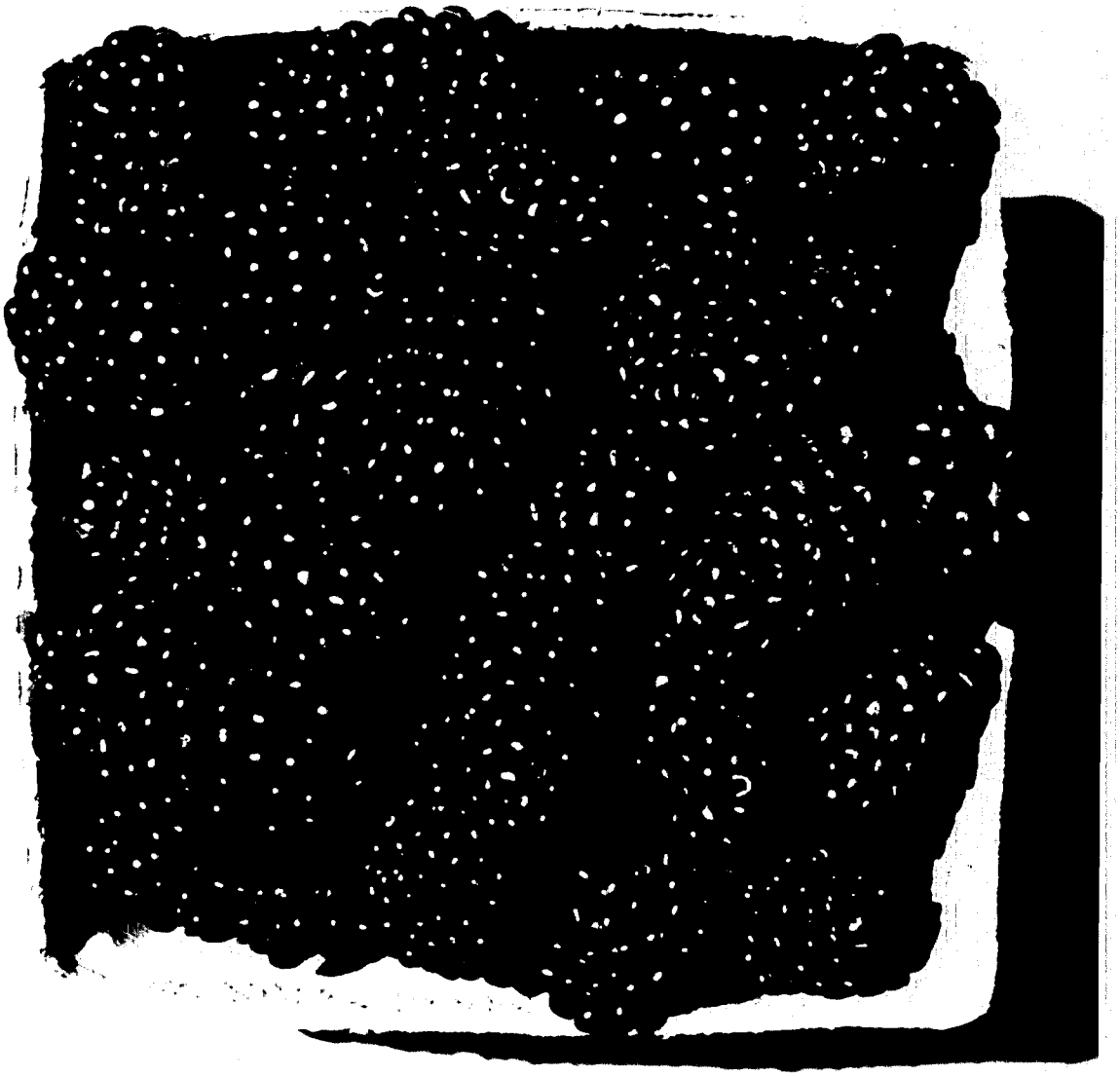

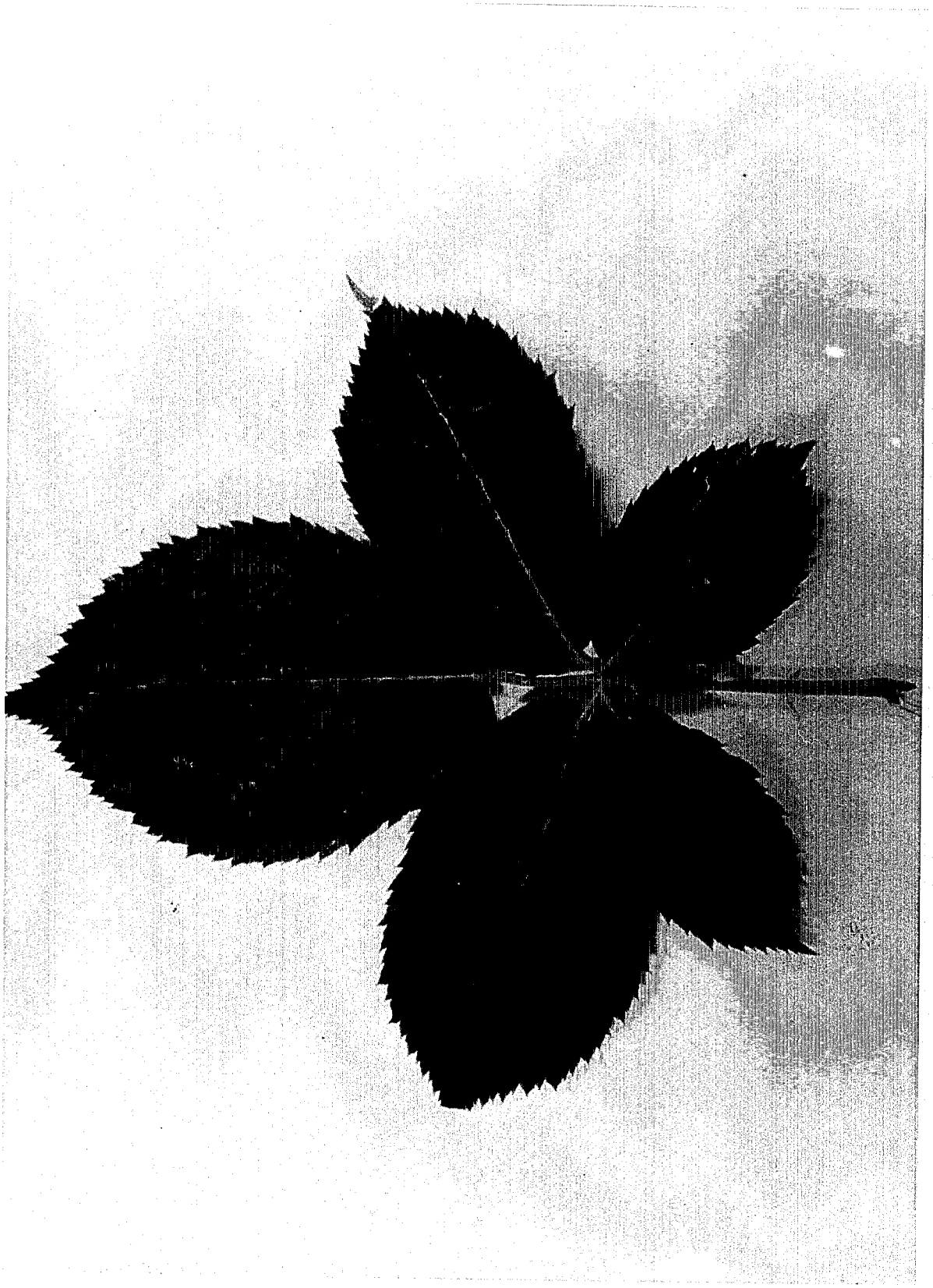

* * * * *